(12) United States Patent
Salamone et al.

(10) Patent No.: US 8,771,972 B2
(45) Date of Patent: Jul. 8, 2014

(54) CLOZAPINE IMMUNOASSAY

(75) Inventors: Salvatore J. Salamone, Stockton, NJ (US); Jodi Blake Courtney, Doylestown, PA (US); Howard Sard, Arlington, MA (US); Christopher Spedaliere, Allentown, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 189 days.

(21) Appl. No.: 13/186,147

(22) Filed: Jul. 19, 2011

(65) Prior Publication Data

US 2012/0301974 A1 Nov. 29, 2012

Related U.S. Application Data

(63) Continuation-in-part of application No. 13/114,252, filed on May 24, 2011, now abandoned.

(51) Int. Cl.
*G01N 33/53* (2006.01)
*G01N 33/543* (2006.01)
*C07K 1/10* (2006.01)
*C07K 17/02* (2006.01)

(52) U.S. Cl.
USPC .......... 435/7.93; 435/7.1; 435/7.92; 436/501; 436/518; 436/523; 436/815; 530/388.9; 530/389.8; 530/402; 530/403

(58) Field of Classification Search
None
See application file for complete search history.

(56) References Cited

U.S. PATENT DOCUMENTS

| | | | |
|---|---|---|---|
| 6,197,764 B1 | 3/2001 | Bradley et al. | |
| 2006/0223134 A1* | 10/2006 | Salamone et al. | ........... 435/7.92 |
| 2006/0252744 A1 | 11/2006 | Burstein | |
| 2009/0215082 A1 | 8/2009 | Salamone et al. | |
| 2012/0301973 A1* | 11/2012 | Salamone et al. | ............ 436/501 |

OTHER PUBLICATIONS

Ming et al., "Therapeutic drug monitoring of clozapine and norclozapine in human serum using ultra-performance liquid chromatography-tandem mass spectrometry," J. Anal. Toxicol., 2009, vol. 33, No. 4, pp. 198-203.*
Mendoza et al., "N-Desmethylclozapine: Is There Evidence for its Antipsychotic Potential?," Clin. Neuropharm., 2009, vol. 32, issue 3, pp. 154-157.*
Gardner et al., "A Comparison of the Covalent Binding of Clozapine and Olanzapine to Human Neutrophils In Vitro and In Vivo," Mol. Pharmacol., 1998, vol. 53, pp. 999-1008.*
Liu et al., "Clozapine is oxidized by activated human neutrophils to a reactive nitrenium ion that irreversibly binds to the cells," J. Pharm. Exper. Therap., 1995, vol. 275, No. 3, pp. 1476-1483.*
Lai et al., "Bioactivation and Covalent Binding of Hydroxyfluperlapine in Human Neutrophils: Implications for Fluperlapine-Induced Agranulocytosis," Drug Metabolism Disposition, 2000, vol. 28, No. 3, pp. 255-263.*
The International Search Report and Written Opinion by the International Searching Authority, issued on Jul. 31, 2012, in the related PCT application No. PCT/US12/36257.

* cited by examiner

*Primary Examiner* — Galina Yakovleva

(57) ABSTRACT

Novel conjugates and immunogens derived from clozapine and antibodies generated by these immunogens are useful in immunoassays for the quantification and monitoring of clozapine in biological fluids.

15 Claims, No Drawings

CLOZAPINE IMMUNOASSAY

CROSS-REFERENCE TO RELATED APPLICATION

This Application is a Continuation-in-Part Application of U.S. application Ser. No. 13/114,252 filed May 24, 2011 now abandoned.

FIELD OF THE INVENTION

This invention relates to the field of immunoassays for determining the presence and/or quantifying the amount of clozapine in human biological fluids in order to rapidly determine optimal drug concentrations during treatment.

BACKGROUND OF THE INVENTION

Schizophrenia is a severe psychiatric disorder affecting approximately 1% of the world's population. Clinical symptoms of schizophrenia include delusions, auditory hallucinations, disorganized thoughts and speech, social withdrawal, lack of motivation, and cognitive dysfunction such as disorganized thinking and memory impairments. This disorder is believed to be caused by a combination of neurological defects including dopamine and serotonin levels, and inhibitory interneuron deficiencies. Schizophrenia can be treated with drugs which target neurotransmitters and receptors, commonly referred to as antipsychotic or neuroleptic drugs.

One class of antipsychotic drug termed "atypical antipsychotics" or more commonly "second generation antipsychotics" includes the tricyclic dibenzazepine derivative, clozapine (I). Clozapine, marketed under Clozaril® by Novartis in the United States, interferes with the binding of dopamine at the dopamine receptors $D_1$, $D_2$, $D_3$, and $D_5$, and has a high affinity for the $D_4$ receptor (Package Insert Clozaril 2009). Clozaril also acts as an antagonist at adrenergic, cholinergic, histaminergic, and serotonergic receptors. Clozapine is almost completely metabolized by cytochrome P450 in humans to the N-desmethyl, and N-Oxide derivatives. The N-desmethyl metabolite has only limited activity, while the N-Oxide derivative is inactive. The activity of N-desmethyl metabolite is with receptors other than the receptors with which clozapine is active.

Clozapine has the following formula:

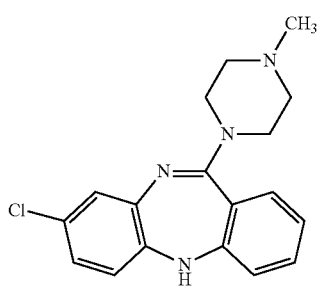

I

N-desmethylclozapine has the following formula:

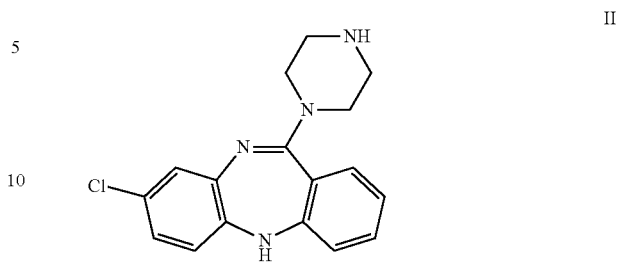

II

Clozapine-N-oxide has the following formula:

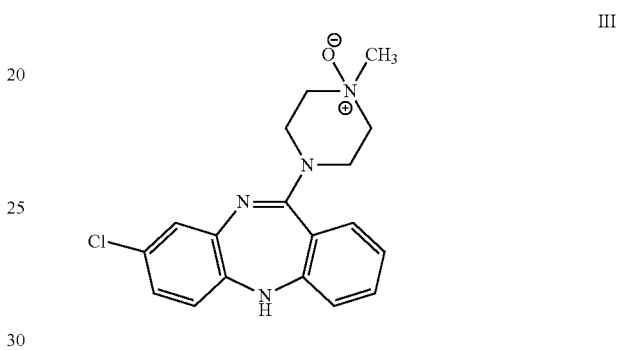

III

Plasma concentration of clozapine is effected by varying cytochrome P450 activity (Chetty, M and M Murray, Curr Drug Metab, 8, 4, 307-13 2007; Mauri, M C, et al., Clin Pharmacokinet, 46, 5, 359-88 2007; Mendoza, M C and J P Lindenmayer, Clin Neuropharmacol, 32, 3, 154-7 2009), age, sex, caffeine use, and smoking (Rostami-Hodjegan, A, et al., J Clin Psychopharmacol, 24, 1, 70-8 2004).

Clozapine has been shown to have high inter-patient variability in plasma steady-state concentrations and this variability can impact safety and quality of life (Mauri, M C, L S Volonteri, A Colasanti, A Fiorentini, I F De Gaspari and S R Bareggi, Clin Pharmacokinet, 46, 5, 359-88 2007).

Since efficacy of clozapine is improved within a specific range of plasma drug concentration and the drug exhibits wide intra-patient pharmacokinetic variability monitoring concentrations of this drug in blood and adjusting to target levels would be of value in increasing efficacy and minimizing toxicity (Mauri, M C, L S Volonteri, A Colasanti, A Fiorentini, I F De Gaspari and S R Bareggi, Clin Pharmacokinet, 46, 5, 359-88 2007)

As a result of this variability, equal doses of the same drug in different individuals can result in dramatically different clinical outcomes. The effectiveness of the same dosage of clozapine varies significantly based upon individual drug clearance and the ultimate serum drug concentration in the patient. Therapeutic drug management would provide the clinician with insight on patient variation in drug administration. With therapeutic drug management, drug dosages could be individualized to the patient, and the chances of effectively treating the disorder without the unwanted side effects would be much higher.

In addition, therapeutic drug management of clozapine would serve as an excellent tool to ensure compliance (Treur, M, et al., BMC Health Serv. Res., 9, 9 2009; Valenstein, M, et al., J. Clin. Psychiatry, 67, 10, 1542-1550 2006) with administration and prescribed dosage to achieve effective serum concentration levels. Routine therapeutic drug management of clozapine would require the availability of simple automated tests adaptable to general laboratory equipment. The use of liquid chromatography (LC) with ultraviolet (UV) or mass spectrometry detection to determine the concentration of clozapine in human blood and plasma has been described (Rosland, M, et al., Drug Dev Ind Pharm, 33, 10, 1158-66 2007; Rao, L V, et al., J Clin Lab Anal, 23, 6, 394-8 2009; Ming, D S and J Heathcote, J Anal Toxicol, 33, 4, 198-203 2009; Niederlander, H A, et al., J Chromatogr B Analyt Technol Biomed Life Sci, 834, 1-2, 98-107 2006). These methods are labor intensive, requiring liquid-liquid or solid phase extractions, use expensive equipment and are not amenable to routine clinical laboratory use. To date, there are no immunoassays for measuring clozapine in human biological fluids of patients treated with this antipsychotic agent.

As seen from the foregoing, there are no immunoassays for determining the presence and/or quantifying the amount of clozapine in human biological fluids. Routine therapeutic drug management of clozapine by immunoassays would provide simple automated tests adapted to standard laboratory equipment. However, in order to provide such immunoassays, antibodies specific to clozapine must be produced. The derivatives and immunogen used in this assay must impart through these corresponding antibodies produced specific reactivity to clozapine without any substantial cross-reactivity reactivity to therapeutically or pharmacologically active or inactive metabolites of clozapine which interfere with the detection of clozapine, these interfering metabolites being N-desmethylclozapine, (the compound of formula II) and clozapine-N-oxide (the compound of formula III). In conducting immunoassays for monitoring clozapine, it is important that the antibodies used not be reactive with the pharmaceutically active metabolite, N-desmethylclozapine (the compound of formula II). This is true since reactivity with N-desmethylclozapine interferes with the detection of clozapine in the patient sample and there is no correlation between the detectable N-desmethylclozapine and clinical outcome. See Y.-Q. Xiang et al. *Serum Concentrations of clozapine and norclozapine in the prediction of relapse of patients with schizophrenia*, Schizophrenia Research, 83 (2006) 201—and M. C. Mendoza & J. P. Lindenmayer. *N-Desmethylclozapine: Is there evidence for its antipsychotic potential?*, Clinical Neuropharmacology 32 (3) 154-157

Therefore, in order to be effective in monitoring drug levels by means of an immunoassay, the antibodies should be specific to clozapine and not cross react with its major pharmaceutically active metabolite, N-desmethylclozapine.

SUMMARY OF INVENTION

In accordance with this invention, a new class of antibodies have been produced which are substantially selectively reactive to clozapine so as to selectively bind to clozapine. By selectively reactive, it is meant that this antibody only reacts with the clozapine and does not substantially react or cross-react with the clozapine metabolites, N-desmethylclozapine and clozapine-N-oxide. Cross-reactivity with these clozapine metabolites prevents an accurate determination by an immunoassay of the presence and the amount of clozapine in human biological fluids. By means of these antibodies, an immunoassay is provided for detecting and quantifying the amount of clozapine in samples of human patients treated with clozapine for monitoring clozapine levels, to prevent overdosing which could cause serious side effects such as agranulocytosis and epileptic seizures.

It has been found that by using immunogens which are conjugates of an immunogenic polyamine polymer with a compound of the formula:

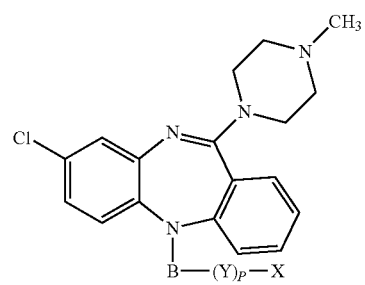

wherein B is: —(C=O)—, —(C=O)—NH—, —(C=O)—O—, —CH2-;
Y is an organic spacing group;
X is a terminal functional group capable of binding to a polyamine polymer; and
p is an integer from 0 to 1;
or salts thereof;
produce antibodies which are specific for clozapine and do not substantially react with or bind to N-desmethylclozapine and clozapine-N-oxide.

The provision of these antibodies which substantially selectively react with clozapine and do not cross react with N-desmethylclozapine and clozapine-N-oxide allows one to produce an immunoassay which can specifically detect and quantify so as to monitor clozapine in the fluid samples of patients being treated with clozapine. Also, included within this invention are reagents and kits for said immunoassay.

DETAILED DESCRIPTION

In accordance with this invention, a new class of antibodies is provided which substantially selectively reacts with clozapine and does not substantially react or cross react with N-desmethylclozapine or clozapine-N-oxide as mentioned hereinabove. It has been discovered that through the use of these derivatives of clozapine of formula IV or salts thereof as immunogens, this new class of antibodies of this invention is provided. It is through the use of these antibodies that an immunoassay, including reagents and kits for such immunoassay for detecting and/or quantifying clozapine in blood, plasma or other body fluid samples has been developed. By use of this immunoassay, the presence and amount of clozapine in body fluid samples of patients being treated this therapeutic agent can be detected and/or quantified. In this manner, a patient being treated with clozapine can be monitored during therapy and his treatment adjusted in accordance with said monitoring. By means of this invention one achieves the therapeutic drug management of clozapine in schizophrenic patients being treated with clozapine as a therapeutic agent. The therapeutic agent to be detected is clozapine of formula I.

The reagents utilized in the assay of this invention are conjugates of a polymeric carrier with the compounds of formula IV. These conjugates are competitive binding partners with the clozapine present in the sample for the binding with the antibodies of this invention. Therefore, the amount of conjugate reagent which binds to the antibody will be inversely proportional to the amount of clozapine in the sample. In accordance with this invention, the assay utilizes any conventional measuring means for detecting and measuring the amount of said conjugate which is bound or unbound to the antibody.

Through the use of said means, the amount of the bound or unbound conjugate can be determined. Generally, the amount of clozapine in a sample is determined by correlating the measured amount of the bound or unbound conjugate produced by the clozapine in the sample with values of the bound or unbound conjugate determined from standard or calibration curve obtained with samples containing known amounts of clozapine, where known amounts are in the range expected for the sample to be tested. These studies for producing calibration curves are determined using the same immunoassay procedure as used for the sample.

DEFINITIONS

Throughout this description the following definitions are to be understood:

The term "Ph" as used throughout this application designates a phenyl radical. The term "alkylene" designates a divalent saturated straight or branch chain hydrocarbon substituent containing from one to ten carbon atoms.

The terms "immunogen" and "immunogenic" refer to substances capable of eliciting, producing, or generating an immune response in an organism.

The term "conjugate" refers to any substance formed from the joining together of separate parts. Representative conjugates in accordance with the present invention include those formed by the joining together of a small molecule, such as the compound of formula IV, and a large molecule, such as a carrier or a polyamine polymer, particularly a protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is clozapine.

As used herein, a "spacing group" or "spacer" refers to a portion of a chemical structure which connects two or more substructures such as haptens, carriers, immunogens, labels, or tracers through a functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join at one or more positions with a hapten, in this case clozapine, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also, various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), ovalbumin, bovine thyroglobulin (BTG) etc. Alternatively, synthetic poly(amino acids) may be utilized.

Immunogenic carriers can also include poly aminopolysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains poly(amino acid) residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with, or otherwise attached to a polyamine polymer to provide one or more reactive sites for bonding to the terminal functional group X in the compounds of the formula IV.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for clozapine. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cerebral spinal fluid, cells, organs, tissues, bone, bone marrow, lymph, lymph nodes, synovial tissue, chondrocytes, synovial macrophages, endothelial cells, and skin.

Reagents and Immunogens

In an immunoassay based upon an antibody, a conjugate of clozapine is constructed to compete with the clozapine in the sample for binding sites on the antibody. In the immunoassay of this invention, the reagents of formula IV are the nitrogen substituted clozapine derivatives formed on the 1-nitro group of clozapine of formula I. In the compounds of formula IV, the linker spacer constitutes the "Y—X" portion of this molecule. This linker X and the spacer—"Y" are conventional in preparing conjugates for immunoassays and immunogens for producing antibodies. Any of the conventional spacer-linking groups utilized to prepare conjugates for immunoassays and immunogens for producing antibodies can be utilized in the compounds of formula IV. Such conventional linkers and spacers are disclosed in U.S. Pat. No. 5,501,987 and U.S. Pat. No. 5,101,015.

The conjugates as well as the immunogens are prepared from the compound of the formula I. In the conjugates or immunogens of the carrier with the hapten, the carriers are linked in one or positions to one or more reactive thio amino groups contained by the polymer portion of the carrier to form the hapten which has the formula:

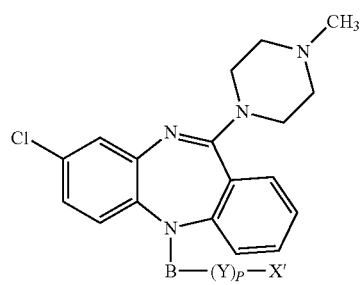

wherein X' is a functional linking group and p and Y are as above;

Among the preferred spacer groups are included the spacer groups hereinbefore mentioned. Particularly preferred spacing groups are groups such as alkylene containing from 1 to 10 carbon atoms,

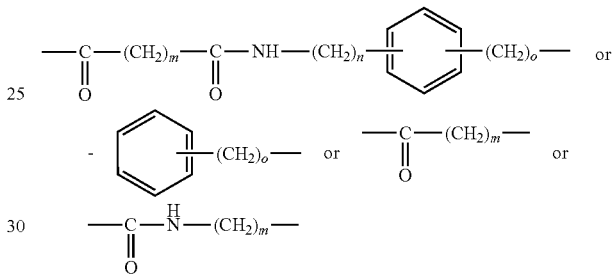

wherein n and o are integers from 0 to 6, and m is an integer from 1 to 6 with alkylene being the especially preferred spacing group.

In the compounds of formula V, where X' is a functional group linking the spacer, preferably through a reactive amine group on the polymeric carrier. The group X' is the result of the terminal functional group X in the compounds of formula IV binding to the reactive amino group in the polyamine polymer of the carrier or the immunogen. Any terminal functional group capable of reacting with an amino group can be utilized as the functional group X in the compounds of formula IV. These terminal functional groups preferably included within X are:

These terminal functional groups preferably included within X are:

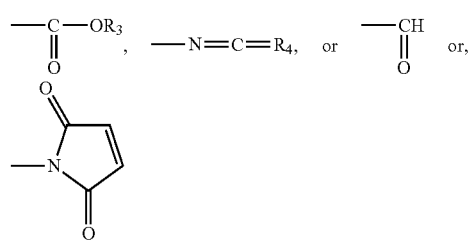

wherein $R_3$ is hydrogen or taken together with its attached oxygen atom forms a reactive ester and $R_4$ is oxygen or sulfur. The —N=C=$R_4$, radical can be an isocyanate or as isothiocyanate. The active esters formed by —OR$_3$ include imidoester, such as N-hydroxysuccinamide, 1-hydroxy benzotriazole and p-nitrophenyl ester. However, any active ester which can react with an amine or thiol group can be used.

The carboxylic group and the active esters are coupled to the carrier or immunogenic polymer by conventional means. The amine group on the polyamine polymer, such as a protein, produces an amide group which connects the spacer to the polymeric immunogens or carrier to form the conjugates of this invention.

When X in the compound of formula IV is

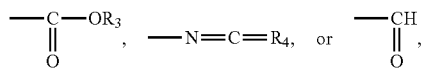

these compounds preferably react with the free amino group of the polymeric or immunogenic carrier. On the other hand, X in the compound of formula IV can be the maleimide radical of the formula

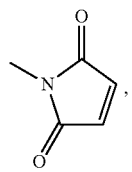

which reacts with both thio or thiol group.

These compounds of formula IV are reacted to attach to a polymeric protein which has been modified to convert an amino group to a thiol group. This can be done by the reacting a free amino group of a polymeric protein carrier with a compound of the formula

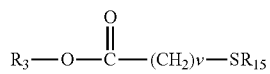
VI wherein $R_{15}$ is a thiol protecting group;
$R_3$ is as above; and
v is an integer of from 1 to 4.

This reaction is carried out in an aqueous medium by mixing the protein containing carrier with the compound of formula VI in an aqueous medium. In this reaction temperature and pressure are not critical and the reaction can be carried out at room temperature and atmospheric pressure. Temperatures of from 10° C. to 25° C. are generally preferred. In the protein containing carrier which is reacted with the compound of Formula VI, any conventional thiol protecting agent can be utilized. The thiol protecting groups are well known in the art with 2-pyridyldthio being the preferred protecting group. By this reaction, the thiol group, SH— becomes the functional group of the carrier which bonds the compound of formula IV to the remainder of the carrier Before reacting with the compound of Formula IV with the thiol modified carrier, the thiol protecting group of the thiol modified carrier is removed by conventional means. Any conventional means for removing a thiol protecting group can be utilized in carrying out this reaction. However, in utilizing a means to remove the thiol protecting group, care must be taken that the reactants be soluble in the aqueous medium and do not in any way destroy or harm the polyamine polymer contained in the carrier. A preferred means for removing this protecting group is by the use of dithiothreitol as an agent to reduce the resultant condensation product. This reduction can be carried out by simply adding the reducing agent to the reaction medium without utilizing higher pressures or temperatures. This reduction can be carried out at room temperature and atmospheric pressure.

While the above method represents one means for converting a reactive terminal amino group on the polyamine polymeric containing carrier to a thiol group, any conventional means for carrying out this conversion can be utilized. Methods for converting terminal amino groups on polyamine polymeric containing carriers to thiol groups are well known in the art and can be employed in accordance with this invention.

The reaction of the polymeric polyamine containing carrier having a terminal reactive thiol group with the compound of formula IV where X is a functional group capable of binding to the terminal thiol group carried by the carrier can be carried out by conventional means. In this embodiment, the compound of formula IV where X is maleimide is reacted with the thiol group carried by the polyamine polymeric carrier. Any well known means for addition of a thiol across a maleimide double bond can be utilized in producing the conjugates of formula IV which are conjugated to the carrier through a thiol bridge.

In accordance with a preferred embodiment, the conjugates, which include the immunogens of the present invention, that are bonded through amide bonds, the chemical bond between the carboxyl group containing Clozapine hapten and the amino groups on the carrier or immunogen can be obtained using a variety of methods known to one skilled in the art. It is frequently preferable to form amide bonds by first activating the carboxylic acid moiety X of the clozapine hapten in the compound of formula IV or their pharmaceutically acceptable salts by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the clozapine hapten of the compound of Formula IV or its pharmaceutically acceptable salts is then reacted in a buffered solution containing the protein carrier.

In preparing the amino bonded conjugates where the clozapine derivative of formula IV contains a primary or secondary amino group as well as the carboxyl group, it is necessary to use an amine protecting group during the activation and coupling reactions to prevent the conjugates from reacting with themselves. Typically, the amines on the clozapine derivative of formula IV are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing clozapine hapten and the reactive amino groups on the polyamine polymer contained by the carrier or immunogen can be established using a variety of methods known to one skilled in the art. It is frequently preferable to form amide bonds. Amide bonds are formed by first activating the carboxylic acid moiety in the compounds of formula IV by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the clozapine hapten of formula V is then reacted with a buffered solution containing the carrier with the reactive amino group.

On the other hand where X is a terminal isocyanate or thioisocyanate radical in the compound of formula IV, these radicals when reacted with the free amine of a polyamine polymer produce the conjugate or immunogen of formula V where X' is

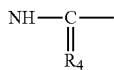

with the amino group on the polyamine carrier or the immunogenic polypeptide.

Where X, in the compounds of formula IV contains an aldehyde radical, these compounds may be connected to the free amino group of the polyamine polypeptide on the carrier through an amine linkage by reductive amination. Any conventional method of condensing an aldehyde with an amine such as through reductive amination can be used to form this linkage. In this case, X' in the ligand portions of formula IV is —$CH_2$—.

The compounds of formula IV are formed by reacting clozapine of formula I with a halide of the formula:

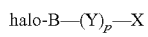

wherein p, B, Y and X are as above.

Any conventional means of reacting a halide with an amine nitrogen can be utilized in condensing the compound of formula IV to the secondary amine nitrogen position on the clozapine of formula I. The use of a halide in the compound of formula IV provides an efficient means for forming such a substituted tertiary amine by condensing the halide with the secondary amine group on the compound of formula I.

Where the compound of formula I is in the form of its salt it is desired to convert this salt to its free base before reacting with the compound of formula IV to form the compound of formula IV. This can be carried out by conventional means such as neutralization of the salt. Where the salt is a basic salt, neutralization can be accomplished in an aqueous media by addition of an acid. Where the salt is an acid addition salt neutralization is accomplished in an aqueous media by addition of a base.

The compound of formula IV can be converted into the immunogens and/or the conjugate reagents of this invention by reacting these compounds with a carrier containing a polyamine or a polypeptide. The same polypeptide can be utilized as the carrier and as the immunogenic polymer in the immunogen of this invention provided that polyamine or polypeptide is immunologically active. However, to form the conjugates, these polymers need not produce an immunological response as needed for the immunogens. In accordance with this invention, the various functional group represented by X' in the compounds of formula V can be conjugated to the carrier containing polymer with a reactive amino group by conventional means of attaching a functional group to an amino group contained within the polymer. In accordance with a preferred embodiment, in the compound of formula IV, X is a carboxylic acid group or an active ester thereof.

The compounds of formula IV as either the reagent, conjugate including the immunogen prepared there from can be present or used in the immunoassay of this invention in its salt form or as a free base. The free amino group in the compound of formula IV and in the conjugate including immunogen prepared there from readily forms salts with acids preferably pharmaceutically acceptable acids Any acid salt of the compound of formula IV and the conjugates including immunogen prepared there from can be used in this invention. These salts including both inorganic and organic acids such as, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids.

Antibodies

The present invention also relates to novel antibodies including monoclonal antibodies to clozapine produced by utilizing the aforementioned immunogens. In accordance with this invention it has been found that these antibodies produced in accordance with this invention are selectively reactive with clozapine and do not react or cross-react with clozapine-N-oxide or N-desmethyl-clozapine which interfere with immunoassays for clozapine. The ability of the antibodies of this invention not to react with N-desmethyl-clozapine or clozapine-N-oxide makes these antibodies provide an immunoassay for detecting the presence and/or quantifying the amount of clozapine in patient fluid samples.

The present invention relates to novel antibodies and monoclonal antibodies to clozapine. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and one or more subsequent booster shots of between 50 and 100 ug immunogen/mouse over a six month period. Through periodic bleeding, the blood samples of the immunized mice were observed to develop an immune response against clozapine binding utilizing conventional immunoassays. These methods provide a convenient way to screen for hosts which are producing antisera having the desired activity. The antibodies were also screened against the major metabolite of N-desmethylclozapine and clozapine-N-oxide, and showed no substantial binding to these compounds.

Monoclonal antibodies are produced conveniently by immunizing Balb/c mice according to the above schedule followed by injecting the mice with either 100 ug immunogen i.p. or i.v. on three successive days or 400 ug immunogen i.p. or i.v. followed by 200 ug daily for the following two days starting four days prior to the cell fusion. Other protocols well known in the antibody art may of course be utilized as well. The complete immunization protocol detailed herein provided an optimum protocol for serum antibody response for the antibody to clozapine or its pharmacologically active salts.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce clozapine or its pharmacologically active salts monoclonal antibodies are formed by the fusion of mouse myeloma cells and spleen cells from mice immunized against clozapine or its pharmacologically active salts-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutagenesis to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are selective for clozapine without having any substantial cross-reactivity with the only clozapine metabolites: N-desmethylclozapine and clozapine-N-oxide. By having no substantial cross-reactivity, it is meant that the antibodies of this invention have no reactivity or cross-reactivity relative to their reactivity with clozapine with these metabolites, particularly N-desmethylclozapine and clozapine-N-oxide of less than 5%, preferably less than 2%, and most preferably less than 1%. These percentages are based upon the reactivity of these antibodies with clozapine.

Immunoassays

In accordance with this invention, the conjugates and the antibodies generated from the immunogens of these compounds of formula IV can be utilized as reagents for the determination of clozapine in patient samples. This determination is performed by means of an immunoassay. Any immunoassay in which the reagent conjugates formed from the compounds of formula IV compete with the clozapine in the sample for binding sites on the antibodies generated in accordance with this invention can be utilized to determine the presence of clozapine in a patient sample. The manner for conducting such an assay for clozapine in a sample suspected of containing clozapine, comprises combining an (a) aqueous medium sample, (b) an antibody to clozapine generated in accordance with this invention and (c) the conjugates formed from the compounds of formula IV or mixtures thereof. The amount of clozapine in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of clozapine. In determining the amount of clozapine in an unknown sample, the sample, the conjugates formed from the compounds of formula IV and the antibody may be added in any order.

Various means can be utilized to measure the amount of conjugate formed from the compounds of formula IV bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the clozapine conjugates formed from the compounds of formula V, these nanoparticles form an aggregate. However, when the antibody coated or absorbed nanoparticles react with the clozapine in the sample, the clozapine from the sample bound to these nanoparticles does not cause aggregation of the antibody nanoparticles. The amount of aggregation or agglutination can be measured in the assay mixture by absorbance.

On the other hand, these assays can be carried out by having either the antibody or the clozapine conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula IV which is bound or unbound with the antibody. Other suitable labels include chromophores, fluorophores, etc.

As a matter of convenience, assay components of the present invention can be provided in a kit, a packaged combination with predetermined amounts of new reagents employed in assaying for clozapine. These reagents include the antibody of this invention, as well as, the conjugates formed from the compounds of formula V.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:
MsCl Methanesulfonyl chloride
DIPEA N—N'-Diisopropylethylamine
$CH_2Cl_2$ chloroform
MeOH methanol
$Na_2SO_4$ sodium sulfate
LiOH lithium hydroxide
EtOAc ethyl acetate
$Et_3N$ triethylamine
THF tetrahydrofuran
TFA trifluoroacetic acid
pTSA p-Toluenesulfonic acid
HATU O-(7-Azabenzotriazol-1-yl)-N,N,N',N'-tetramethyluronium hexafluorophosphate
DMF Dimethylformamide
DMSO Dimethylsulfoxide
s-NHS sulfo-N-hydroxy succinimide
EDC 1-(3-dimethylaminopropyl)-3-ethylcarbodiimide hydrochloride
KLH Keyhole Limpet HemocyaninBSA Bovine serum albumin
PBS Phosphate buffered saline
NaCl sodium chloride
HRP horse radish-peroxidase
ANS 8-Anilino-1-naphthalenesulfonic acid
TMB 3,3',5,5'-Tetramethylbenzidine
TRIS Tris(hydroxymethyl)aminomethane hydrochloride
di H2O deionized water The phosphate buffer composition has an aqueous solution containing
15.4 mM Sodium phosphate dibasic ($Na_2HPO_4$)
4.6 mM Sodium phosphate monobasic ($NaH_2PO_4$)
pH=7.2±0.10

In the following Examples, Schemes 1-2 below set forth the specific compounds prepared and referred to by numbers in the Examples. The schemes are as follows:

Scheme 1

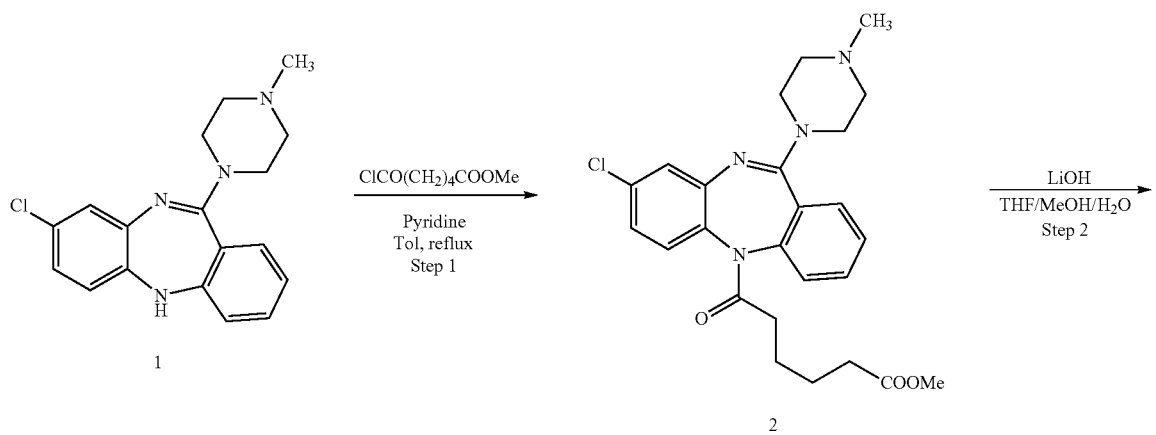

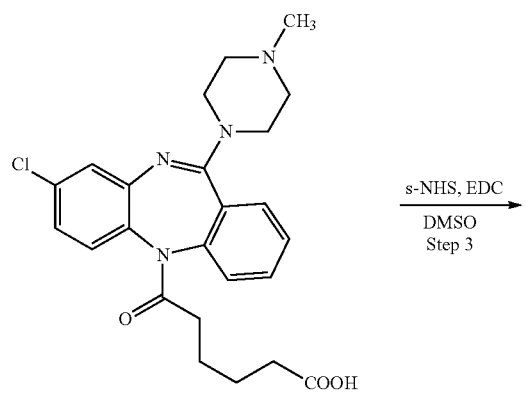

-continued
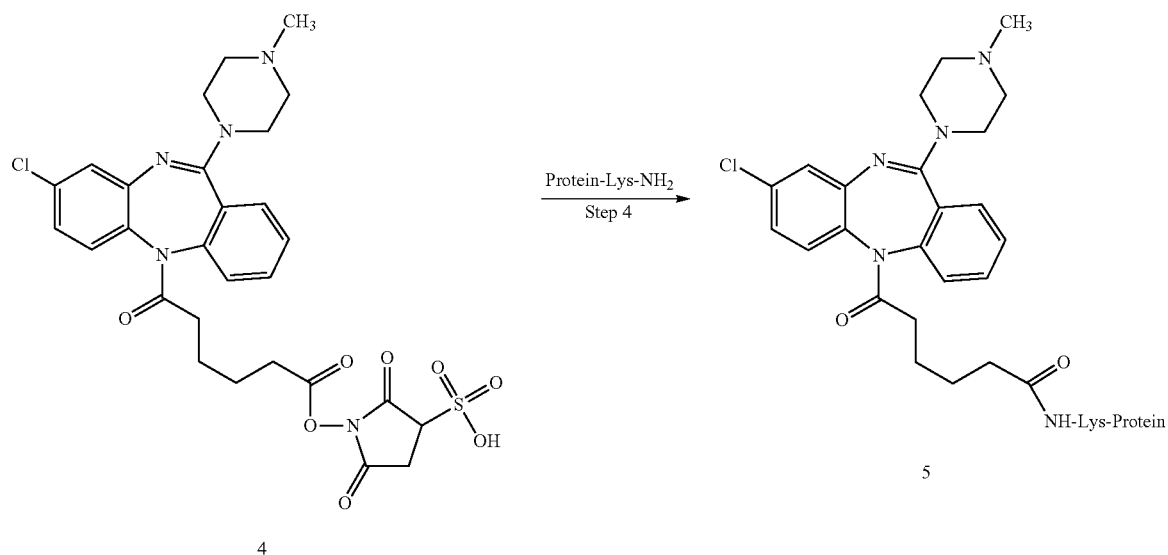
Scheme 2
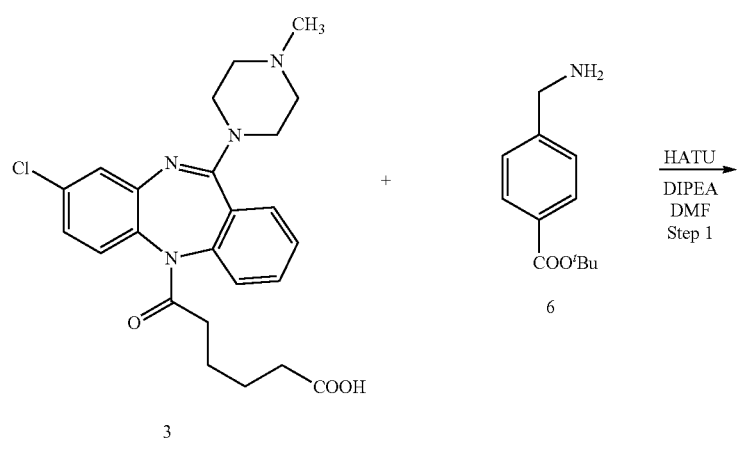
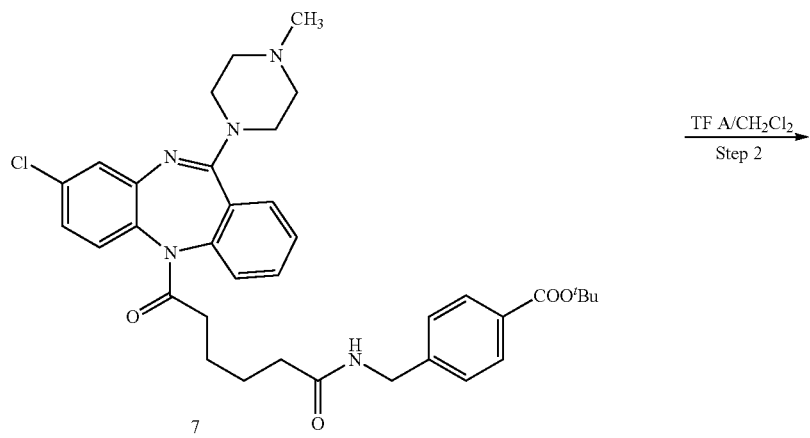

-continued
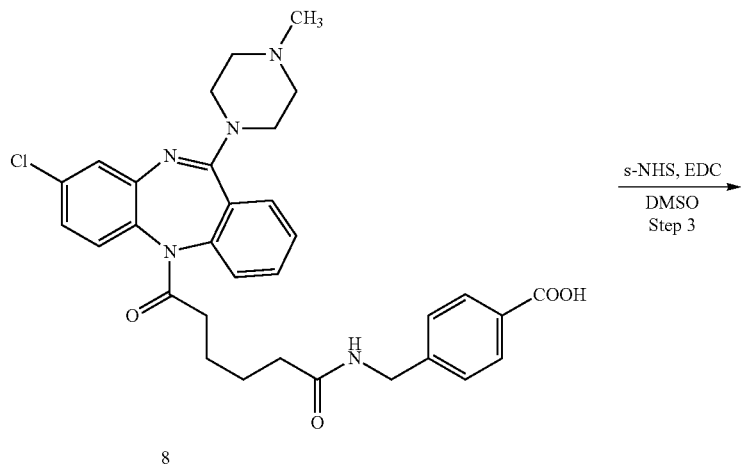
8
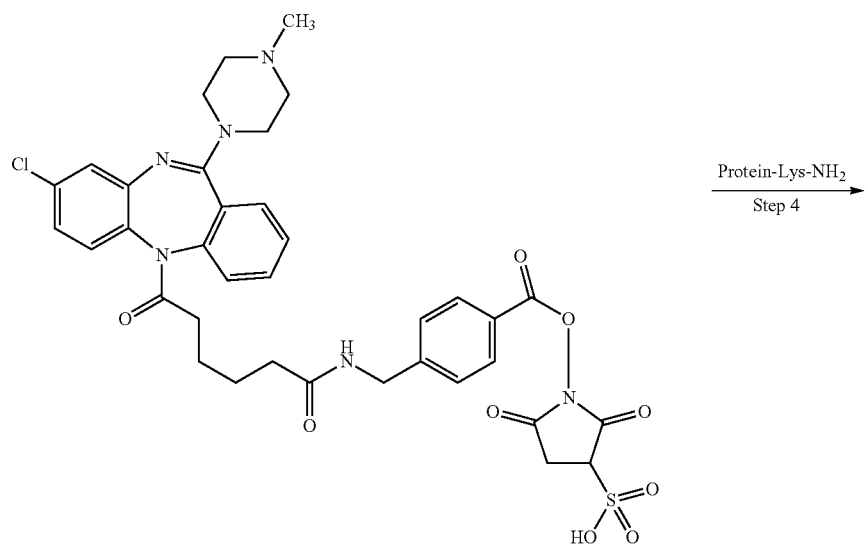
9
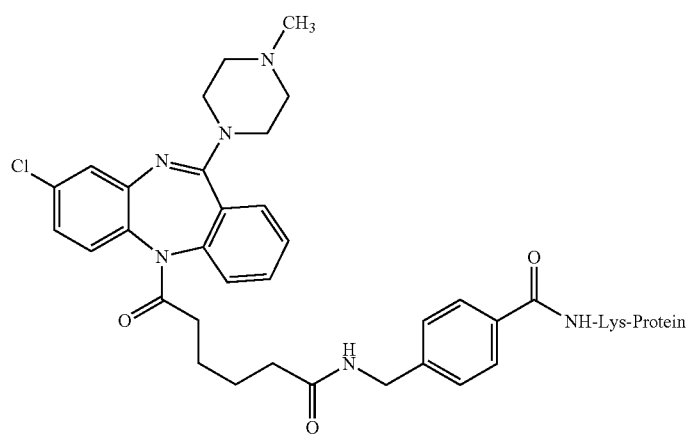
10

Example 1

Preparation of 6-[8-Chloro-11-(4-methyl-piperazin-1-yl)-dibenzo[b,e]-[1,4]diazepin-5-yl]-6-oxo-hexanoic acid (Scheme 1)

To a solution of compound [1] (2 g, 6.12 mmol) in toluene (60 mL), pyridine (0.49 mL, 6.12 mmol) was added followed by methyl adipoyl chloride (1.3 mL, 7.95 mmol). The reaction mixture was heated at reflux for 3.5 h, cooled to ambient temperature and stirred with 10% aq. $Na_2CO_3$ (12 mL) for 20 min. The reaction mixture was diluted with ether and washed with water. The organic phase was dried ($Na_2SO_4$), filtered and evaporated. Purification by flash chromatography using $CH_2Cl_2$/MeOH98:2 to 97:3 containing 0.1% $Et_3N$ afforded compound [2] (3.07 g, quantitative).

To a mixture of compound [2] (3.06 g, 6.12 mmol), THF (50 mL), MeOH (50 mL) and $H_2O$ (19 mL), $LiOH.H_2O$ (1.8 g, 42.84 mmol) was added and the reaction mixture was stirred at ambient temperature under nitrogen for 3 h, after which the TLC showed the absence of starting material. The reaction mixture was diluted with EtOAc and washed with 0.1 N HCl. The aqueous layer was re-extracted with $CH_2Cl_2$ (3×). The EtOAc and $CH_2Cl_2$ layers were separately washed with sat. brine, dried using anhyd. $Na_2SO_4$, filtered and evaporated. The combined product was triturated with $CH_2Cl_2$/hexane to afford compound [3], which is 6-[8-Chloro-11-(4-methyl-piperazin-1-yl)-dibenzo[b,e]-[1,4]diazepin-5-yl]-6-oxo-hexanoic acid (2.50 g, 90%).

Example 2

Preparation of 4-({6-[8-Chloro-11-(4-methyl-piperazin-1-yl)-dibenzo[b,e]-[1,4]diazepin-5-yl]6-oxo-hexanoylamino}-methyl)-benzoic acid tert-butyl ester (Scheme 2)

At 0° C., to a mixture of compound [3], 6-[8-Chloro-11-(4-methyl-piperazin-1-yl)-dibenzo[b,e]-[1,4]diazepin-5-yl]-6-oxo-hexanoic acid (600 mg, 1.32 mmol), compound [6] (430 mg, 1.45 mmol), DIPEA (0.78 mL, 4.48 mmol) in dry DMF (13 mL), HATU (601 mg, 1.58 mmol) was added and the reaction mixture was stirred overnight. An additional amount of HATU (601 mg, 1.58 mmol) was added and the reaction mixture was stirred at ambient temperature for 1 day. The reaction mixture was partitioned between water and EtOAc, the organic layer was successively washed with 1 N HCl, sat. $NaHCO_3$, water and sat. brine, and dried using anhyd. $Na_2SO_4$, filtered and evaporated. Purification by chromatography using $CH_2Cl_2$/MeOH/$Et_3N$ (93:7:0.1) afforded compound [7] (638 mg, 75%).

At ambient temperature, to a solution of compound [7] (635 mg, 0.986 mmol) in $CH_2Cl_2$ (4 mL), TFA (4 mL) was added and the reaction mixture was stirred at ambient temperature under nitrogen for 4 h. The solvent was evaporated and co-evaporated with $CH_2Cl_2$ (2×) and dried under vacuum. The residue on trituration with ether afforded compound [8], which is 4-({6-[8-Chloro-11-(4-methyl-piperazin-1-yl)-dibenzo[b,e]-[1,4]diazepin-5-yl]6-oxo-hexanoylamino}-methyl)-benzoic acid tert-butyl ester (563 mg, 97%).

Example 3

General Method for Preparing s-NHS Activated Drug Derivatives from the Corresponding Acids [3] & [8]

In Examples 3a and 3b, clozapine acid derivatives [3] & [8] were activated with EDC and s-NHS to produce the s-NHS activated esters of clozapine [4] & [9] for eventual conjugation to proteins (examples 4 and 5).

Example 3a

Preparation of s-NHS activated 6-[8-Chloro-11-(4-methyl-piperazin-1-yl)-dibenzo[b,e]-[1,4]diazepin-5-yl]-6-oxo-hexanoic acid [4]

Clozapine derivative [3], Example 1, Scheme 1, (56.8 mg) was dissolved in 5.68 mL of DMSO to which was added s-NHS (66.56 mg) and EDC (58.58 mg). The reaction mixture was stirred for 20 hours at ambient temperature under a nitrogen atmosphere to produce the s-NHS activated ester of clozapine [4]. The reaction mixture was used directly in Examples 4 and 5a.

Example 3b

Preparation of s-NHS activated 4-({6-[8-Chloro-11-(4-methyl-piperazin-1-yl)-dibenzo[b,e]-[1,4]diazepin-5-yl]6-oxo-hexanoylamino}-methyl)-benzoic acid [9]

Clozapine derivative [8], Example 2, Scheme 2 (25.0 mg) was dissolved in 2.5 mL of DMSO to which was added s-NHS (19.9 mg) and EDC (17.6 mg). The reaction mixture was stirred for 20 hours at ambient temperature under a nitrogen atmosphere to produce the s-NHS activated ester of clozapine [9]. The reaction mixture was used directly in Example 5b.

Example 4

Preparation of KLH Immunogen [5] with Activated Hapten [4]

A protein solution of KLH was prepared by dissolving 300 mg of KLH in 20 mL of phosphate buffer (50 mM, pH 7.5), followed by addition of 40.85 mL of s-NHS activated clozapine derivative [4] prepared in Example 3a. The reaction mixture of KLH and activated clozapine derivative [4] was allowed to stir for 20 hours at room temperature to produce the clozapine-KLH conjugate [5]. The clozapine-KLH conjugate [5] was then purified by dialysis against 30% DMSO in phosphate buffer (50 mM, pH 7.5) at room temperature. Thereafter the DMSO proportion was reduced stepwise: 20%, 10% and 0%. The last dialysis was performed against phosphate buffer at 4° C. The clozapine-KLH conjugate [5] was characterized by ultraviolet-visible (UV-VIS) spectroscopy. The conjugate was diluted to a final concentration of 2 mg/mL in phosphate buffer (50 mM, pH 7.5).

Example 5a

Preparation of BSA Conjugate [5] with Activated Hapten [4]

A protein solution of BSA was prepared by dissolving 1 g BSA in phosphate buffer (50 mM, pH 7.5) for a final concentration of 50 mg/mL. To this protein solution was added 0.83 mL of s-NHS activated clozapine derivative [4] prepared in Example 3a. The amount of s-NHS activated clozapine derivative [4] added to the protein solution of BSA was calculated for a 1:1 molar ratio between the derivative of clozapine [4] and BSA. The mixture of BSA and activated clozapine derivative [4] was allowed to stir for 18 hours at room temperature to produce the conjugate of the activated clozapine ester and BSA. This conjugate was then purified by dialysis against 20% DMSO in phosphate buffer (50 mM, pH 7.5) at room temperature. Thereafter the DMSO proportion was reduced stepwise: 10% and 0%. The last dialysis was performed against phosphate buffer at 4° C. The purified clozapine-BSA [5] conjugate was characterized by UV/VIS spectroscopy.

Example 5b

Preparation of BSA Conjugate [10] with Activated Hapten [9]

A protein solution of BSA was prepared by dissolving 1 g BSA in phosphate buffer (50 mM, pH 7.5) for a final concentration of 50 mg/mL. To 10.0 mL of the protein solution of BSA while stirring on ice, was added 0.620 mL of s-NHS activated clozapine derivative [9] prepared in Example 3b. The amount of s-NHS activated clozapine derivative [9] added to the protein solution of BSA was calculated for a 1:1 molar ratio between the derivative of clozapine [9] and BSA. The mixture of BSA and activated clozapine derivative [9] was allowed to stir for 18 hours at room temperature to produce the conjugate of the activated clozapine ester and BSA [10]. This conjugate was then purified by dialysis against 15% DMSO in phosphate buffer (50 mM, pH 7.5) at room temperature. Thereafter the DMSO proportion was reduced stepwise: 10%, 5%, and 0%.

The last dialysis was performed against phosphate buffer at 4° C. The purified clozapine-[9]-BSA conjugate was characterized by UV/VIS spectroscopy.

Example 6a

Preparation of Polyclonal Antibodies to Clozapine-KLH Conjugate [5]

Ten female BALB/c mice were immunized i.p. with 100 µg/mouse of clozapine-KLH immunogen [5], as prepared in Example 4, emulsified in Complete Freund's adjuvant. The mice were boosted once, four weeks after the initial injection with 100 µg/mouse of the same immunogen emulsified in Incomplete Freund's Adjuvant. Twenty days after the boost, test bleeds containing polyclonal antibodies from each mouse were obtained by orbital bleed. The anti-serum from these test-bleeds containing clozapine antibodies are evaluated in Examples 8 and 9.

Example 6b

Preparation of Monoclonal Antibodies to Clozapine-KLH [5]

Mice from Example 6a that were immunized with clozapine-[5]-KLH prepared in example 4 were used to produce monoclonal antibodies. For monoclonal antibodies starting three days before the fusion, the mice were injected i.p. with either 400 µg (3 days before fusion), 200 µg (2 days before fusion), and 200 µg (1 day before fusion) or 100 µg (3 days before fusion), 100 µg (2 days before fusion), and 100 µg (1 day before fusion) of clozapine-KLH conjugate [5] in PBS/DMSO prepared in example 4. Spleen cells were isolated from the selected mice and fused with $2 \times 10^7$ SP2/0 cells with 50% polyethylene glycol 1500 according to the method of Coligan, J. E. et al., eds., Current Protocols in Immunology, 2.5.1-2.5.8, (1992), Wiley & Sons, NY. The fused cells were plated on ten 96-well plates in DMEM/F12 supplemented with 20% FetalClone I, 2% L-glutamine (100 mM) and 2% 50×HAT. Two to three weeks later, the hybridoma supernatant was assayed for the presence of anti-clozapine antibodies by ELISA (as in example 8). Cells from the wells that gave positive ELISA results (example 8) were expanded to 24 well plates. Clones positive by ELISA were subcloned twice by limiting dilution according to the method disclosed in Coligan, J. E. et al., eds., Current Protocols in Immunology, 2.5.8-2.5.17, 1992, Wiley & Sons, NY. Hybridoma culture supernatants containing monoclonal antibody from selected subclones were confirmed for clozapine binding by a competitive ELISA (Example 9). These monoclonal antibodies were tested for clozapine binding and cross-reactivity to the major clozapine metabolites, N-desmethylclozapine and clozapine-N-oxide, by indirect competitive microtiter plate assay as described in Example 9.

Example 7a

Microtiter Plate Sensitization Procedure with Clozapine-BSA Conjugate [5]

The ELISA method for measuring clozapine concentrations was performed in polystyrene microtiter plates (Nunc MaxiSorp F8 Immunomodules) optimized for protein binding and containing 96 wells per plate. Each well was coated with Clozapine-BSA Conjugate [5] (prepared as in Example 5a) by adding 300 µL of Clozapine-BSA Conjugate [5] at 10 µg/mL in 0.05M sodium carbonate, pH 9.6, and incubating for three hours at room temperature. The wells were washed with 0.05M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 7b

Microtiter Plate Sensitization Procedure with Clozapine-BSA Conjugate [10]

The ELISA method for measuring clozapine concentrations was performed in polystyrene microtiter plates (Nunc MaxiSorp F8 Immunomodules) optimized for protein binding and containing 96 wells per plate. Each well was coated with Clozapine-BSA Conjugate [10] (prepared as in Example 5b) by adding 300 µL of Clozapine-BSA Conjugate [10] at 10 µg/mL in 0.05M sodium carbonate, pH 9.6, and incubating for three hours at room temperature. The wells were washed with 0.05M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 8

Antibody Screening Procedure—Titer

This procedure is to find the dilution of antibody to be tested for displacement as in Example 9. The ELISA method for screening clozapine antibodies was performed with the microtiter plates that were sensitized with clozapine-BSA conjugate prepared in Examples 7a and 7b. The antibody screening assay was performed by diluting the murine serum from test bleeds containing polyclonal clozapine antibodies to 1:10, 1:10,00 and 1:10,000 (volume/volume) in phosphate buffered saline containing 0.1% BSA and 0.01% thimerosal. To each well of clozapine-BSA sensitized wells (prepared in Examples 7a and 7b) 50 μL phosphate buffered saline containing 0.1% BSA and 0.01% thimerosal and 50 μL of diluted antibody were added and incubated for 10 minutes at room temperature with shaking. During this incubation antibody binds to the clozapine-BSA conjugate passively absorbed in the wells (Examples 7a and 7b). The wells of the plates were washed three times with 0.02 M TRIS, 0.9% NaCl, 0.5% Tween-80 and 0.001% thimerosal, pH 7.8 to remove any unbound antibody. To detect the amount of clozapine antibody bound to the clozapine-BSA conjugate in the wells, 100 μL of a goat anti-mouse antibody—HRP enzyme conjugate (Jackson Immunoresearch) diluted to a specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to clozapine antibodies in the wells, the plates were again washed three times to remove unbound goat anti-mouse antibody—HRP enzyme conjugate. To develop a measurable color in the wells washing was followed by the addition of 100 μL of TMB (TMB Substrate, BioFx), the substrate for HRP, to develop color during a 10 minute incubation with shaking at room temperature. Following the incubation for color development, 50 μL of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing antibody dilution of the antibody measured (x-axis) IVs. absorbance 650 nm (y-axis) and interpolating the titer at an absorbance of 1.5. The titer which produced absorbance of 1.5 determined the concentration (dilution) of antibody used in the indirect competitive microtiter plate assay described in Example 9.

Example 9

Indirect Competitive Microtiter Plate Immunoassay Procedure Determining $IC_{50}$ and Cross-Reactivity for Antibodies to Clozapine The ELISA method for determining $IC_{50}$ values and cross-reactivity was performed with the microtiter plates that were sensitized with clozapine-BSA conjugates as described in Examples 7a and 7b. The analytes were diluted as follows: clozapine was serially diluted in DMSO and further diluted to 1% DMSO over a concentration range of 0.01 to 50 ng/mL for clozapine-[5]-BSA and clozapine-[10]-BSA microtiter plates, N-desmethylclozapine was serially diluted in DMSO and further diluted to 1% DMSO over a concentration range of 0.24 to 1,000 ng/mL for clozapine-BSA conjugate [5] and clozapine-BSA conjugate [10] microtiter plates, and clozapine-N-oxide was serially diluted in DMSO and further diluted to 1% DMSO over a concentration range of 0.24 to 1,000 ng/mL for clozapine-BSA conjugate [5] and clozapine-BSA conjugate [10] microtiter plates. Each of the assays were performed by incubating 50 μL of the analyte solution with 50 μL of one of the antibodies selected from the polyclonal antibodies produced in Example 6 with the immunogen of Example 4. The assays were all performed by diluting the concentration of the antibodies in each of the wells to the titer determined in Example 8. During the 10 minute incubation (at room temperature with shaking) there is a competition of antibody binding for the clozapine-BSA conjugate in the well (produced in Examples 7a and 7b) and the analyte in solution. Following this incubation the wells of the plate were washed three times with 0.02 M TRIS, 0.9% NaCl, 0.5% Tween-80 and 0.001% thimerosal, pH 7.8 to remove any material that was not bound. To detect the amount of clozapine antibody bound to the clozapine-BSA conjugate in the wells (produced in Examples 7a and 7b), 100 μL of a goat anti-mouse antibody—HRP enzyme conjugate (Jackson Immunoresearch) diluted to a predetermined specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to clozapine antibodies in the wells, the plates were again washed three times to remove unbound secondary conjugate. To develop a measurable color in the wells washing was followed by the addition of 100 μL of TMB (TMB Substrate, BioFx), the substrate for HRP, to develop color in a 10 minute incubation with shaking at room temperature. Following the incubation for color development, the absorbance was determined at 650 nm (Molecular Devices Plate Reader). The amount of antibody in a well was proportional to the absorbance measured and inversely proportional to the amount of clozapine in the sample. The $IC_{50}$ values of clozapine were determined by constructing dose-response curves with the absorbance in the wells plotted versus analyte concentration in the wells. The absorbance of the color in the wells containing analyte was compared to that with no analyte and a standard curve was generated. The $IC_{50}$ value for a given analyte was defined as the concentration of analyte that was required to have 50% of the absorbance of the wells containing no analyte. The cross-reactivity was calculated as the ratio of the $IC_{50}$ for clozapine to the $IC_{50}$ value for either N-desmethylclozapine or clozapine-N-oxide and expressed as a percent. After screening the library of monoclonal antibodies using this method, the monoclonal antibodies were chosen. These chosen antibodies were classified according to their plate and well number as follows: 5B1-24-30, 5H2-6-14, 5H2-6-30, 5G10-19-19, 1G9-22-5, and 20A5-25-24. When measured, the percent cross-reactivities of these antibodies to their reactivity with clozapine for N-desmethylclozapine (NDMC) and clozapine-N-oxide were ≤2%. The results for monoclonal antibodies to clozapine are given in Tables I & II below.

TABLE I

Cross-reactivity of competitive immunoassay using monoclonal antibodies to clozapine

| | Plates coated with Clozapine-BSA conjugate [5] (Example 7A) | | | | |
|---|---|---|---|---|---|
| Subclone # | Clozapine IC50 (ng/mL) | NDMC IC50 (ng/mL) | Clozapine-N-oxide IC50 (ng/mL) | % cross-reactivity NDMC | % cross-reactivity N-oxide |
| 5B1-24-30 | 10 | 760 | >1000 | 1.3 | 0.99 |
| 5H2-6-14 | 5 | 920 | 880 | 0.53 | 0.56 |
| 5H2-6-30 | 5 | >1000 | 620 | <0.45 | 0.73 |
| 5G10-19-19 | 0.8 | 150 | 170 | 0.49 | 0.44 |
| 1G9-22-5 | 0.6 | 280 | 40 | 0.22 | 1.39 |
| 20A5-25-24 | 0.7 | >1000 | 100 | <0.07 | 0.72 |

TABLE II

Cross-reactivity of competitive immunoassay using monoclonal antibodies to clozapine.

| Subclone # | Clozapine IC50 (ng/mL) | NDMC IC50 (ng/mL) | Clozapine-N-oxide IC50 (ng/mL) | % cross-reactivity NDMC | % cross-reactivity N-oxide |
|---|---|---|---|---|---|
| 5B1-24-30 | 7 | 600 | 200 | 1.1 | 3.3 |
| 5H2-6-14 | 3 | 970 | 620 | 0.30 | 0.47 |
| 5H2-6-30 | 3 | >1000 | 480 | <0.27 | 0.57 |
| 5G10-19-19 | 2 | 180 | 280 | 1.2 | 0.78 |
| 1G9-22-5 | 0.5 | 220 | 60 | 0.23 | 0.86 |
| 20A5-25-24 | 2 | >1000 | 150 | <0.24 | 1.56 |

As seen from these tables, the antibodies of this invention are substantially selectively reactive with the active form of clozapine and are not substantially cross-reactive with the active metabolites N-desmethylclozapine and clozapine-N-oxide.

The invention claimed is:

1. An immunoassay for detecting clozapine in a sample comprising providing a mixture of a) said sample, b) an antibody selectively reactive with clozapine and not substantially cross-reactive with N-desmethylclozapine and clozapine-N-oxide, and c) a conjugate of a carrier having either a reactive thiol or amino group with a compound of the formula:

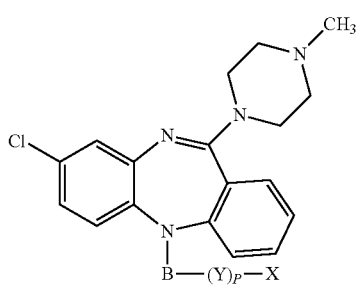

IV wherein B is: —(C=O)—, —(C=O)—NH—, —(C=O)—O—, —CH2-;

Y is an organic spacing group;

X is a terminal functional group capable of binding to said carrier; and p is an integer from 0 to 1;

or salts thereof;

causing the clozapine in the sample and said conjugate in said mixture to bind with said antibody and thereafter measuring the amount of said conjugate in said mixture which is bound or unbound to said antibody whereby the presence of clozapine in the sample can be determined.

2. The immunoassay of claim 1, wherein the sample is a human sample.

3. The immunoassay of claim 2, wherein said antibody is generated from an immunogen comprising an immunogenic carrier having a reactive thiol or amino group conjugated to a compound of the formula:

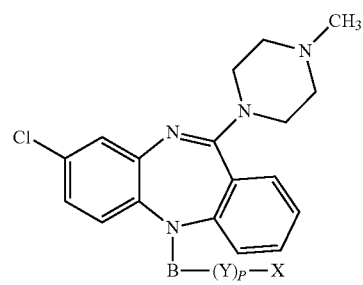

IV wherein B is: —(C=O)—, —(C=O)—NH—, —(C=O)—O—, —CH2-;

Y is an organic spacing group;

X is a terminal functional group capable of binding to said immunogenic carrier; and p is an integer from 0 to 1;

or salts thereof.

4. The immunoassay of claim 3, wherein said immunogenic carrier has a reactive thiol group and X in the compound which is conjugated to said immunogenic carrier is a terminal functional group capable of binding to said reactive thiol group.

5. The immunoassay of claim 4, wherein X is

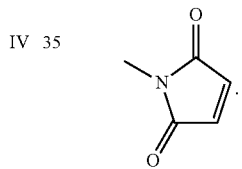

6. The immunoassay of claim 5, wherein Y is $C_1$-$C_{10}$ alkylene.

7. The immunoassay of claim 6 wherein the immunogenic carrier contains as the functional group

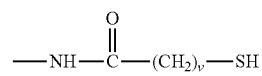

wherein v is an integer from 1 to 6.

8. The immunoassay of claim 2, wherein the antibody is attached to a solid support.

9. The immunoassay of claim 8, wherein the solid support is microtiter plates.

10. The immunoassay of claim 9, wherein the solid support is nanoparticles.

11. A kit for determining the presence of clozapine in a patient sample comprising reagents in separate containers, one of the reagents being a conjugate of a carrier having either a reactive thiol or amino group with a compound of the formula:

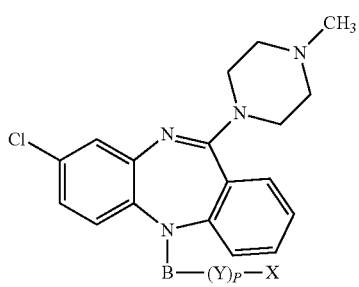

IV wherein B is: —(C=O)—, —(C=O)—NH—, —(C=O)—O—, —CH₂—;

Y is an organic spacing group;

X is a terminal functional group capable of binding to said carrier; and p is an integer from 0 to 1;

or salts thereof; and the second container containing an antibody selectively reactive with clozapine and not substantially cross-reactive with N-desmethylclozapine and clozapine-N-oxide.

12. The kit of claim 11, wherein said conjugate is present in a predetermined amount in said first container.

13. The kit of claim 12, wherein said kit is used to determine the amount of clozapine in said sample.

14. The kit of claim 13, wherein said carrier has a reactive thiol group and X is a terminal functional group capable of binding to said reactive thiol group.

15. The kit of claim 14, wherein X is

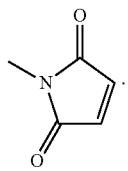

* * * * *